United States Patent [19]

Harth et al.

[11] 4,209,504

[45] Jun. 24, 1980

[54] TOOTHPASTE WITH ZEOLITE POLISHING AGENT

[75] Inventors: Helmut Harth, Mainz; Dieter Becker, Darmstadt Wixhausen, both of Fed. Rep. of Germany

[73] Assignee: Blendax-Werke R. Schneider GmbH & Co., Mainz, Fed. Rep. of Germany

[21] Appl. No.: 971,224

[22] Filed: Dec. 20, 1978

[30] Foreign Application Priority Data

Dec. 22, 1977 [DE] Fed. Rep. of Germany ....... 2757290

[51] Int. Cl.$^2$ .......................... A61K 7/16; A61K 7/18; A61K 7/22; A61K 7/28
[52] U.S. Cl. ........................................ 424/49; 424/50; 424/52; 424/54; 424/56; 424/57
[58] Field of Search .................................. 424/49–58, 424/357

[56] References Cited

U.S. PATENT DOCUMENTS 4,132,771  1/1979  Schreiber et al. ..................... 424/52

FOREIGN PATENT DOCUMENTS 378010  7/1923  Fed. Rep. of Germany .
332142  7/1930  United Kingdom .

*Primary Examiner*—Shep K. Rose
*Attorney, Agent, or Firm*—Connolly and Hutz

[57] ABSTRACT

A toothpaste composition contains an alkali metal aluminum silicate zeolite as the polishing agent base. The composition is non-corrosive to aluminum containers, polishes well without excessive abrasion and is compatible with dental fluorine compounds. A particularly suitable polishing agent is Zeolite A having the empirical formula $Na_{12}(AlO_2)_{12}.(SiO_2)_{12}.27H_2O$.

5 Claims, No Drawings

TOOTHPASTE WITH ZEOLITE POLISHING AGENT

The present invention relates to a tooth paste which has no corrosive effect against bare (unlacquered) aluminum surfaces and which contains synthetic zeolite of the alkali aluminum silicate type as the sole and preponderant polishing agent.

In a tooth paste, the polishing agent quantitatively is the most important constituent aside from water and the moistureholding agents. The best known polishing agents used in tooth pastes are calcium carbonate, the various calcium phosphates, such as dicalcium orthophosphate and calcium pyrophosphate in particular, insoluble alkali metaphosphate, precipitated silicon dioxide gel, either in the form of a hydrogel or of the dried xerogel. These cleaning substances as well as aluminum hydroxide, having come into use because of their refractive indices make them useful particularly in the preparation of transparent and translucent tooth pastes.

The further numerous substances proposed as polishing agents in tooth pastes essentially have not achieved practical importance but rather represent merely "paper prior art."

A substance suitable as a polishing agent in tooth pastes must have a certain abrasiveness (the cleaning or polishing capacity) without damaging the tooth enamel. In other words the agent should be sufficeintly abrasive in order to remove the plaque existing on human teeth and to clean the interdental spaces without affecting tooth enamel or dentin or excessively irritating the gums.

Furthermore, the polishing agent should be compatible with the active substances used in tooth pastes nowadays, particular value being placed on an inert effect on the fluorine compounds, such as alkali fluorides and alkali monofluorophosphates, notoriously used in tooth pastes nowadays.

A further desirable property for polishing agents in tooth pastes in particular and tooth paste constituents in general is to act non-corrosively with polished aluminum surfaces. Since numerous polishing agents have a corrosive effect on aluminum, it is necessary to provide the tooth paste tubes to be used with an inner protective lacquer. The lacquer increases the cost for the packaging material and consequently also for the finished tooth paste. It can also lead to "knobbing" of the toothpaste tubes and consequently to reclamation upon possible damage of the inner protective lacquer film.

It has now been found that a non-corrosive polishing agent, compatible well with fluorine compounds and polishing well yet not excessively abrasive, is obtained by use of a polishing agent comprising more than 50% synthetic zeolite of the alkali aluminum silicate type.

The zeolites per se have been known for a long time. They are used as molecular filters, for water softening and recently also in washing preparations as substitutes for phosphates otherwise used as inorganic builders. The zeolites are watercontaining framework silicates which can be expressed by the general formula $x(M.AlO_2).ySiO_2, zH_2O$, wherein M is alkali metal or ammonium, x is a number between 1 and 64, y is a number dependent on x with the determination of y being one-fold to six-fold of x, and z is a number between 0 and 256.

The synthetic zeolites used in tooth pastes as polishing agents according to the invention may be prepared in a simple known manner from aluminum hydroxide and alkali silicates such as water glass. A product particularly suitable within the scope of the present invention is Zeolite A with the empirical formula $Na_{12}(AlO_2)_{12}.(SiO_2)_{12}.27H_2O$. Such a product is sold by the company Degussa under the trade name "Sasil" and has an average particle size of about 4 microns, an apparent density of about 400 g/l and a loss on ignition of about 20% (1 h at 800° C.). The zeolites being used are insoluble in water. Their average standard particle size is preferably between about 1 and about 30 microns. A summary of the preparation and the properties of the alkali aluminum silicates being used according to the invention is given by F. Schwochow and L. Puppe, "Angewandte Chemie" (Applied Chemistry) 87 (1975), pp. 659–667.

From German published application No. 2,146,224 there are known transparent and translucent tooth pastes which contain a synthetic amorphous complex alkali or alkaline earth aluminum silicate as the cleaning substance which has a refractive index of about 1.44 to 1.47. The alkali aluminum silicates described there differ essentially from the products used in this invention, however, since they are not synthetic zeolites. Furthermore, the subject matter of the German published application is completely different with respect to the object of the present invention which is to produce a toothpaste having an anticorrosive polishing agent with optimum polishing capability and fluoride compatibility. Also, the novel tooth pastes of this invention are not transparent or translucent.

British Pat. No. 332 142 describes tooth powder containing a zeolite of a composition defined not more precisely than calcium ion complex formers. This reference makes no mention of the corrosion-preventive or polishing properties of this zeolite in tooth paste tubes because problems of corrosion do not occur with tooth powders.

The same is true for the disclosure of German Pat. No. 378 010 wherein the zeolites suggested there for use in tooth cleaning agents of unknown origin and composition are used because of their complexing effect on alkaline earth ions.

These patents have nothing in common with the object of this invention and even less with the solution of the problem according to the present invention.

The quantity of polishing agent in the tooth paste is at least 15 and at most 60% by weight and as a rule is preferably about 25 and about 40% by weight.

Although according to the invention the sole application of the alkali aluminum silicate polishing agent of the zeolite A type is preferred, it is possible in principle to add to these polishing agents small amounts of further polishing agents without deteriorating the positive properties of the zeolite. However, such additional polishing agents may not amount to more than 50% by weight of the total polishing agent composition. Polishing agents which may be used in small quantities together with the zeolite are, for example, the various calcium phosphates such as dicalcium phosphate in its anhydrous or hydrated form, calcium pyrophosphate and tricalcium phosphate, silica gels such as silicon dioxide hydrogel or silicon dioxide xerogels as they are sold particularly by the company Grace GmbH under the name "Syloid," calcium carbonate, aluminum hydroxide, finely divided pulverulent synthetic substances or insoluble alkali metaphosphate.

Used as moisture-holding agents are glycerine, polyglycols with a low molar weight or sugar alcohols such as sorbite, mannite and xylite.

Tooth pastes furthermore contain thickening agents. Best suitable as such are the alkali salts of carboxymethyl cellulose, particularly sodium carboxymethyl cellulose; hydroxyalkyl cellulose, particularly hydroxyethyl cellulose; plant gum, such as tragacanth; gum arabic; caraya gum; and Irish moss; synthetic polyelectrolyte such as sodium, potassium or ammonium salt of polyacrylic acid; and also inorganic thickening agents, e.g. colloidal magnesium aluminum silicate.

The proportion of the thickening agent is about 0.25 to 5% by weight of the tooth paste.

A further often-used constituent of tooth pastes comprises surface-active substances.

Suitable as such in particular are water-soluble salts of higher alkyl sulfates, e.g. sodium lauryl sulfate; aliphatic acylamides of saturated monoaminocarboxylic acids, preferably sodium-N-lauroylsarcosinate, taurin fatty acidamides, e.g. sodium-N-alkyl-N-myristoyl tauride; salts of sulfonated monoglycerides of higher fatty acids, e.g. sodium monoglyceride sulfonate; fatty acid esters of isethionic acid and the salts thereof; nonionic surfaceactive agents such as alkylene oxide condensates with fatty alcohols and mono or polyvalent amines; sugar esters, e.g. saccharose monolaurate, sorbitol polyoxyethylene stearate; long-chain amine oxides- e.g. dimethyllauryl amino oxide; ampholytical surfaceactive agents, e.g. betains or long-chain alkylaminocarboxylic acids and cation-active surface-active agents, e.g. quaternary ammonium compounds such as cetyl trimethyl ammonium bromide.

The proportion of surface-active compounds in the novel tooth-cleaning composition is at 0 to about 5% by weight of the total composition.

Tooth-cleaning compositions normally contain aromatic and flavoring substances, preserving agents, and so forth. Those materials are known per se and are described in numerous publications.

As already indicated, the polishing agents in a base of a synthetic zeolite used in the novel tooth-cleaning composition have an excellent compatibility with ionic or complex-bound fluorine. It is therefore a preferred embodiment of the invention to use such fluorine compounds in the novel tooth-cleaning composition, preferably in such quantities as for the concentration of pure fluorine in the substance to amount to about 0.01 to about 1% by weight and preferably 0.1 to 0.5% by weight of the tooth-cleaning composition.

Suitable fluorine compounds are particularly the various salts of monofluorophosphoric acid, particularly sodium, potassium, lithium, calcium and aluminum mono and difluorophosphate, as well as the various fluorides containing fluorine in ionic-bound form, particularly alkalifluorides such as sodium, lithium, potassium and ammonium fluoride, stannous fluoride, manganese fluoride, zirconium fluoride and aluminum fluoride as well as compositions or addition products of these fluorides among themselves or with other fluorine compounds, e.g. potassium or sodium manganese fluoride.

Other fluorides usable within the scope of the present invention are zinc fluoride, germanium fluoride, palladium fluoride, titanium fluoride, alkalifluorozirconates, e.g. sodium or potassium fluorozirconate, stannous fluorozirconate, fluoroborate or fluorosulfate, e.g. sodium or potassium fluorosulfate.

Organic fluorine compounds can also be used successfully, particularly the known addition products of long-chain amines or amino acids and hydrogen fluoride, monoethanolaminohydrofluoride or methyltriethyl ammonium fluoride.

The tooth-cleaning compositions of the invention may contain further substances, known per se, for use in such compositions, e.g. enzymes such as proteases and carbohydrases such as amylase, dextranase, levanase or α-1,3-glucane-3-glucanohydrolase, plaque-removing substances such as the phosphonic acids suggested for this purpose, e.g. hydroxyethane-1,1-diphosphonic acid, or the bisbiguanides 1,6-di-4'-(chlorophenyldiguanido) hexane, 1,6-di-4'-(fluorophenyldiguanido) hexane and 1,6-di-(2-ethylhexyldiguanido) hexane or the preferably water-soluble salts thereof, known under the names "chlorhexidin," "fluorhexidin" or "Alexidin."

A detailed summary of the preparation of the tooth-cleaning compositions and the substances used therein is given in the manual by M. S. Balsam and E. Sagarin, "Cosmetics Science and Technology," 2nd Ed., Vol. 1, pp. 423–532 (1972).

Below are several examples of the tooth-cleaning agents composed in accordance with the invention:

EXAMPLE 1

| | | |
|---|---|---|
| carboxymethyl cellulose | 1.30% | by weight |
| p-hydroxybenzoic acid methyl ester | 0.10% | " |
| glycerine | 20.00% | " |
| aroma | 1.00% | " |
| 1,2-propylene glycol | 2.00% | " |
| benzoic acid | 0.50% | " |
| saccharin sodium | 0.05% | " |
| alkali monofluorophosphate | 0.75% | " |
| sodium aluminum silicate (zeolite A, $Na_{12}(AlO_2)_{12}(SiO)_{12} \cdot 27H_2O$) | 35.00% | by weight |
| pyrogenic silicic acid | 2.50% | " |
| titanium dioxide | 0.70% | " |
| water | 34.30% | " |

The sodium aluminum silicate in the exemplary compositions may be entirely or partially replaced also by the corresponding respective potassium or lithium compound.

The particle sizes of the zeolite used according to the invention are in the range customary for tooth paste polishing agents of between about 1 to about 20 microns and preferably between 2 and 10 microns.

EXAMPLE 2

| | | |
|---|---|---|
| hydroxyethyl cellulose | 1.20% | by weight |
| p-hydroxybenzoic acid ester | 0.08% | " |
| sorbitol, 70% | 7.00% | " |
| benzoic acid | 0.30% | " |
| 1,2-propylene glycol | 3.00% | " |
| aroma | 1.00% | " |
| saccharin sodium | 0.04% | " |
| medicinal soap | 0.60% | " |
| pyrogenic silicic acid | 0.20% | " |
| alkali monflurophosphate | 0.75% | " |
| sodium aluminum silicate (zeolite A, $Na_{12}(AlO_2)_{12}(SiO_2)_{12} \cdot 27H_2O$) | 25.00 | " |
| calcium carbonate | 20.00% | " |
| water | 40.83% | " |

EXAMPLE 3

| | | |
|---|---|---|
| carrageenate | 0.70% | by weight |
| para-hydroxybenzoic acid propyl ester | 0.02% | " |

-continued

| | | |
|---|---|---|
| para-hydroxybenzoic acid methyl ester | 0.05% | " |
| benzoic acid | 0.20% | " |
| glycerine | 18.00% | " |
| 1,2-propylene glycol | 2.00% | " |
| aroma | 1.00% | " |
| saccharin sodium | 0.04% | " |
| alkali monofluorophosphate | 0.75% | " |
| pyrogenic silicic acid | 1.50% | " |
| insoluble Na-metaphosphate | 20.00% | " |
| sodium aluminum silicate ($Na_2O \cdot Al_2O_3 \cdot 2SiO_2 \cdot 4,5H_2O$) | 25.00% | " |
| sodium lauroyl sarcosinate | 1.50% | " |
| water | 29.24% | " |

EXAMPLE 4

| | | |
|---|---|---|
| carboxymethyl cellulose | 1.20% | by weight |
| p-hydroxybenzoic acid methyl ester | 0.07% | " |
| benzoic acid | 0.20% | " |
| sorbitol, 70% | 18.00% | " |
| glycerine | 6.00% | " |
| aroma | 1.00% | " |
| saccharin sodium | 0.05% | " |
| alkali monofluorophosphate | 0.75% | " |
| dicalcium phosphate ($CaHPO_4$) | 10.00% | " |
| sodium aluminum silicate | 2.00% | " |
| pyrogenic silicic acid | 2.00% | " |
| pigment | 0.03% | " |
| water | 30.00% | " |

We claim:
1. In an aqueous toothpaste composition having about 15-60% by weight polishing agent, the improvement comprises said polishing agent containing at least 50% by weight of a synthetic alkali aluminum silicate zeolite of the formula $x(M \cdot AlO_2) \cdot ySiO_2 \cdot zH_2O$, wherein M is alkali metal or ammonium, x is a number between 1 and 64, y is a number dependent on X with the determination of y being one-fold to six-fold of x, and z is a number between 0 and 256.
2. The toothpaste composition according to claim 1 wherein the polishing agent is 100% said zeolite.
3. The toothpaste according to claim 1 wherein said zeolite is a sodium aluminum silicate zeolite.
4. The toothpaste according to claim 1 wherein said zeolite has the empirical formula $Na_{12}(AlO_2)_{12} \cdot (SiO_2)_{12} \cdot 27H_2O$.
5. The toothpaste according to claim 1 wherein the zeolite has a particle size of about 1 to about 30 microns.

* * * * *